(12) United States Patent
Marnfeldt et al.

(10) Patent No.: US 9,446,243 B2
(45) Date of Patent: Sep. 20, 2016

(54) PATIENT POSTURE DETERMINATION AND STIMULATION PROGRAM ADJUSTMENT IN AN IMPLANTABLE STIMULATOR DEVICE USING IMPEDANCE FINGERPRINTING

(71) Applicant: Boston Scientific Neuromodulation Corporation, Valencia, CA (US)

(72) Inventors: Goran N. Marnfeldt, Valencia, CA (US); Jordi Parramon, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 113 days.

(21) Appl. No.: 14/024,276

(22) Filed: Sep. 11, 2013

(65) Prior Publication Data

US 2014/0163638 A1    Jun. 12, 2014

Related U.S. Application Data

(60) Provisional application No. 61/734,629, filed on Dec. 7, 2012.

(51) Int. Cl.
| | |
|---|---|
| *A61N 1/36* | (2006.01) |
| *A61N 1/37* | (2006.01) |
| *A61B 5/053* | (2006.01) |
| *A61B 5/11* | (2006.01) |

(Continued)

(52) U.S. Cl.
CPC ............. *A61N 1/36128* (2013.01); *A61B 5/04* (2013.01); *A61B 5/0538* (2013.01); *A61B 5/1116* (2013.01); *A61N 1/36071* (2013.01); *A61N 1/36139* (2013.01); *A61N 1/3702* (2013.01); *A61B 5/0492* (2013.01)

(58) Field of Classification Search
None
See application file for complete search history.

(56) References Cited

U.S. PATENT DOCUMENTS

| 5,031,618 A | 7/1991 | Mullett |
| 5,233,984 A | 8/1993 | Thompson |

(Continued)

OTHER PUBLICATIONS

Invitation to Pay Additional Fees regarding corresponding PCT Application No. PCT/US2013/060160, dated Jan. 8, 2014.

(Continued)

*Primary Examiner* — Brian T Gedeon
*Assistant Examiner* — Ankit D Tejani
(74) *Attorney, Agent, or Firm* — Lewis, Reese & Nesmith, PLLC (57) ABSTRACT

Methods and circuitry for determining an implanted-neurostimulator patient's position, and adjusting a situation program delivered by the neurostimulator based on the determined position, is disclosed. Impedance measurements of the patient's tissue are taken at the neurostimulator's electrodes, which measurements can comprise complex impedance measurements (magnitude and phase) taken at different frequencies. Such impedance measurements, which can be taken interleaved with stimulation therapy, are used to determine an "impedance fingerprint." This fingerprint can be compared to other known fingerprints stored in the IPG, which known fingerprints are associated with particular stimulation programs. When a measured fingerprint matches one stored in the IPG, the stimulation program associated with the stored fingerprint is automatically used for patient therapy. As different measured fingerprints are encountered, the IPG can learn and store a new stimulation program for such fingerprint by remembering stimulation parameters selected by the patient when such fingerprint is encountered.

38 Claims, 9 Drawing Sheets

(51) Int. Cl.
*A61B 5/04* (2006.01)
*A61B 5/0492* (2006.01)

(56) References Cited

U.S. PATENT DOCUMENTS

| | | | |
|---|---|---|---|
| 5,342,409 A | 8/1994 | Mullett |
| 5,782,884 A | 7/1998 | Stotts et al. |
| 6,044,297 A | 3/2000 | Sheldon et al. |
| 6,659,968 B1 | 12/2003 | McClure |
| 6,993,384 B2 | 1/2006 | Bradley et al. |
| 7,317,948 B1 | 1/2008 | King et al. |
| 7,366,572 B2 | 4/2008 | Heruth et al. |
| 7,395,113 B2 | 7/2008 | Heruth et al. |
| 7,406,351 B2 | 7/2008 | Wesselink |
| 7,447,545 B2 | 11/2008 | Heruth et al. |
| 7,463,927 B1 | 12/2008 | Chaouat |
| 7,491,181 B2 | 2/2009 | Heruth et al. |
| 7,519,431 B2 | 4/2009 | Goetz et al. |
| 7,590,455 B2 | 9/2009 | Heruth et al. |
| 7,706,889 B2 | 4/2010 | Gerber et al. |
| 7,715,920 B2 | 5/2010 | Rondoni et al. |
| 7,717,848 B2 | 5/2010 | Heruth et al. |
| 7,720,548 B2 | 5/2010 | King |
| 7,769,464 B2 | 8/2010 | Gerber et al. |
| 7,801,619 B2 | 9/2010 | Gerber et al. |
| 7,822,481 B2 | 10/2010 | Gerber et al. |
| 7,957,814 B2 | 6/2011 | Goetz et al. |
| 8,032,229 B2 | 10/2011 | Gerber et al. |
| 8,108,049 B2 | 1/2012 | King |
| 8,121,694 B2 | 2/2012 | Molnar et al. |
| 8,121,702 B2 | 2/2012 | King |
| 8,126,567 B2 | 2/2012 | Gerber et al. |
| 8,131,358 B2 | 3/2012 | Moffitt et al. |
| 8,150,530 B2 | 4/2012 | Wesselink |
| 8,150,531 B2 | 4/2012 | Skelton |
| 8,155,753 B2 | 4/2012 | Wesselink |
| 8,175,720 B2 | 5/2012 | Skelton et al. |
| 8,192,398 B2 | 6/2012 | Hoendervoogt et al. |
| 8,200,335 B2 | 6/2012 | Donofrio et al. |
| 8,200,340 B2 | 6/2012 | Skelton et al. |
| 8,209,028 B2 | 6/2012 | Skelton et al. |
| 8,219,206 B2 | 7/2012 | Skelton et al. |
| 8,231,555 B2 | 7/2012 | Skelton et al. |
| 8,231,556 B2 | 7/2012 | Skelton et al. |
| 8,233,992 B2 | 7/2012 | Zhu et al. |
| 8,249,718 B2 | 8/2012 | Skelton et al. |
| 8,282,580 B2 | 10/2012 | Skelton et al. |
| 8,287,520 B2 | 10/2012 | Drew et al. |
| 8,290,593 B2 | 10/2012 | Libbey et al. |
| 8,290,596 B2 | 10/2012 | Wei et al. |
| 8,355,797 B2 | 1/2013 | Caparso et al. |
| 8,571,671 B2 | 10/2013 | Shah et al. |
| 8,639,351 B2 | 1/2014 | Parker et al. |
| 8,676,331 B2 | 3/2014 | Parker |
| 2004/0215286 A1 | 10/2004 | Stypulkowski |
| 2006/0241357 A1* | 10/2006 | Chirife .............. A61N 1/36521 600/301 |
| 2007/0043394 A1* | 2/2007 | Zhang .................. A61N 1/3621 607/8 |
| 2007/0129774 A1 | 6/2007 | Bourget et al. |
| 2007/0191901 A1* | 8/2007 | Schecter .............. A61N 1/3627 607/17 |
| 2007/0208394 A1 | 9/2007 | King et al. |
| 2007/0249968 A1 | 10/2007 | Miesel et al. |
| 2007/0250121 A1 | 10/2007 | Miesel et al. |
| 2007/0255118 A1 | 11/2007 | Miesel et al. |
| 2008/0109050 A1 | 5/2008 | John |
| 2008/0188909 A1 | 8/2008 | Bradley |
| 2009/0024189 A1 | 1/2009 | Lee et al. |
| 2010/0137944 A1 | 6/2010 | Zhu |
| 2011/0060387 A1 | 3/2011 | King et al. |
| 2011/0301665 A1 | 12/2011 | Mercanzini et al. |
| 2011/0319769 A1 | 12/2011 | Hedberg et al. |
| 2012/0083709 A1 | 4/2012 | Parker et al. |
| 2013/0116752 A1 | 5/2013 | Parker et al. |

OTHER PUBLICATIONS

Medtronic. "About Spinal Cord Stimulation," Spinal Cord Stimulation. Online Abstract. Nov. 8, 2012. Medtronic, Inc.

Medtronic. "Understanding Uncomfortable Stimulation," The Continuous Choices of Motion. Online Abstract. Nov. 8, 2012. Medtronic, Inc.

Medtronic. "Features and Specifications," Restore Sensor Neurostimulator, Spinal Cord Stimulation. Online Abstract. Nov. 8, 2012. Medtronic, Inc.

Medtronic. "Advanced Pain Therapy Using Neurostimulation for Chronic Pain". Online Abstract. Nov. 29, 2012. Medtronic, Inc. Minneapolis, MN USA.

International Search Report and Written Opinion regarding corresponding PCT Application No. PCT/US2013/060160, dated May 26, 2014.

"General Programming Guide Neurostimulators for Chronic Pain," Medtronic Inc., http://www.medtronic.com.hk/wcm/groups/mdtcom_sg/@mdt/@neuro/documents/documents/scs-ref-gd-nvsn-prog.pdf, 2013, 65 pages.

* cited by examiner

Figure 4A (patient prone)

Figure 4B (patient bending forward)

PATIENT POSTURE DETERMINATION AND STIMULATION PROGRAM ADJUSTMENT IN AN IMPLANTABLE STIMULATOR DEVICE USING IMPEDANCE FINGERPRINTING

CROSS-REFERENCE TO RELATED APPLICATIONS

This is a non-provisional application claiming priority to U.S. Provisional Patent Application Ser. No. 61/734,629, filed Dec. 7, 2012, which is incorporated herein by reference in its entirety.

FIELD OF THE INVENTION

The present invention relates to implantable stimulator devices, such as spinal cord stimulators.

BACKGROUND

Figures 1A, 1B:
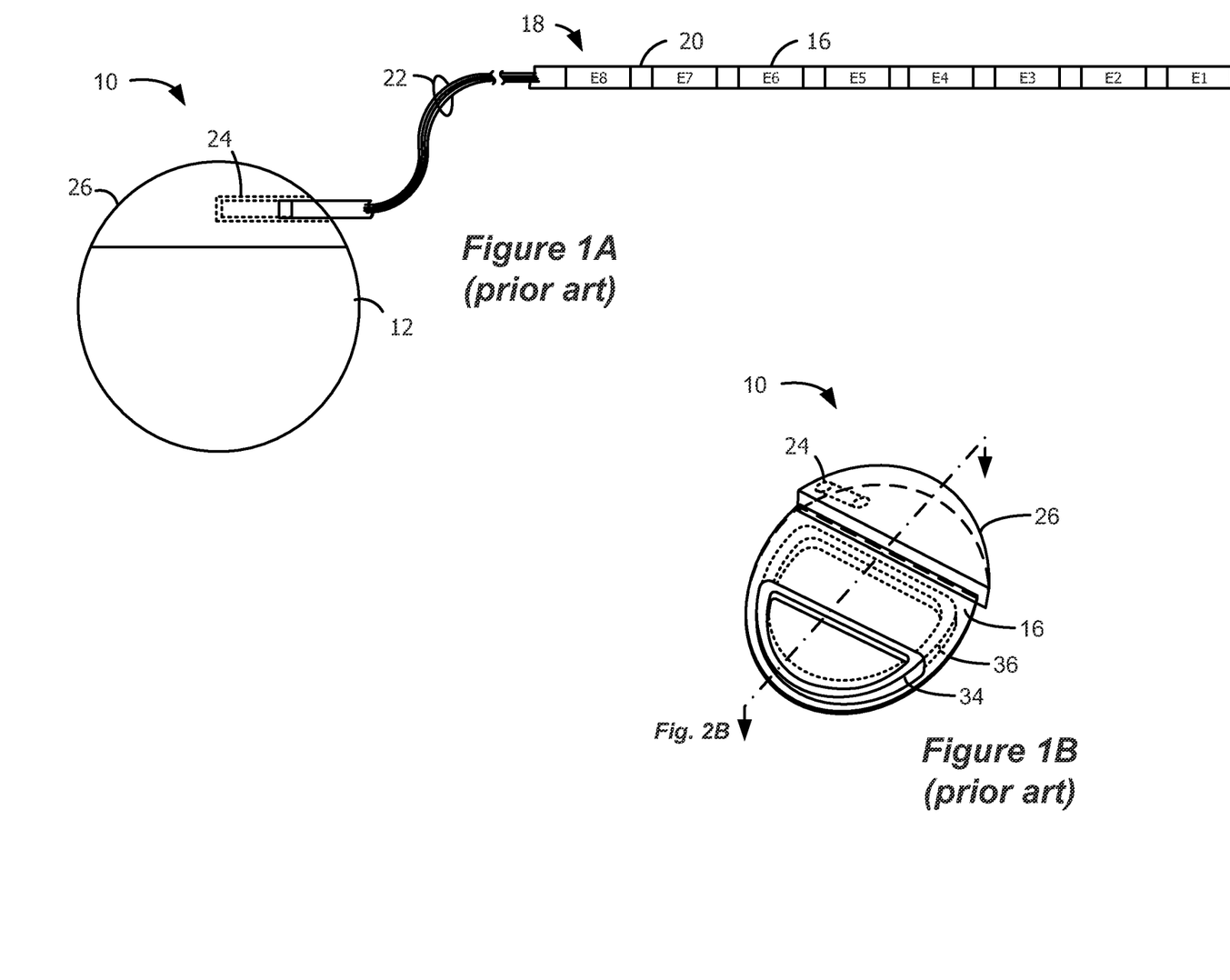
FIGS. 1A-1B show different views of an implantable medical device, specifically an Implantable Pulse Generator (IPG).

Implantable stimulation devices are devices that generate and deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system to treat lower back pain, such as that disclosed in U.S. Pat. No. 6,516,227. However, the present invention may find applicability in any implantable stimulator device As shown in FIGS. 1A-1C, a SCS system typically includes an Implantable Pulse Generator (IPG) 10, which includes a biocompatible device case 12 formed of a conductive material such as titanium for example. The case 12 typically holds the circuitry and battery 14 (FIG. 2B) necessary for the IPG to function, although IPGs can also be powered via external RF energy and without a battery. The IPG 10 is coupled to electrodes 16 via one or more electrode leads 18, such that the electrodes 16 form an electrode array. The electrodes 16 are carried on a flexible body 20, which also houses the individual signal wires 22 coupled to each electrode. In the illustrated embodiment, there are eight electrodes on lead 18, labeled $E_1$-$E_8$. However, the number of electrodes on a lead, as well as the number of leads, are application specific and therefore can vary. The lead 18 couples to the IPG 10 using a lead connector 24, which is fixed in a non-conductive header material 26, which can comprise an epoxy for example.

Figure 2A:
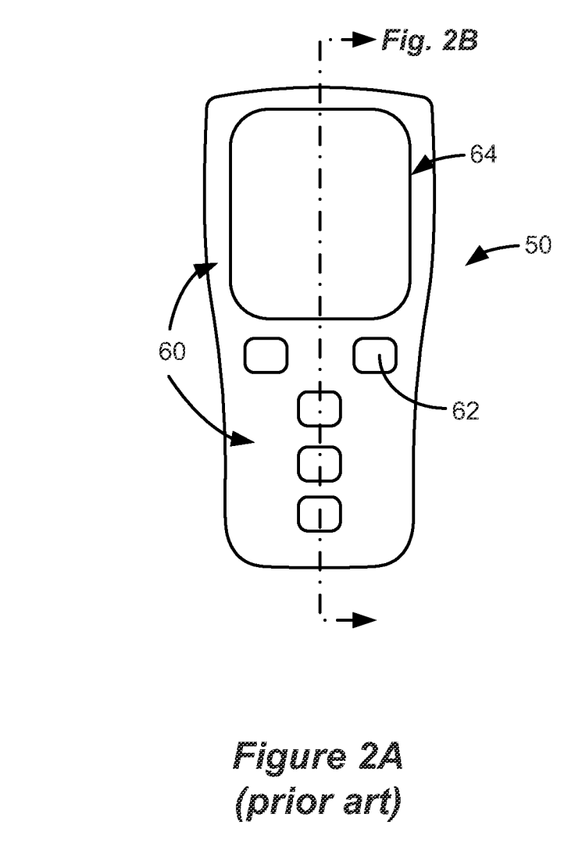
FIGS. 2A-2B show an external controller for communicating with the IPG.
Figure 2B:
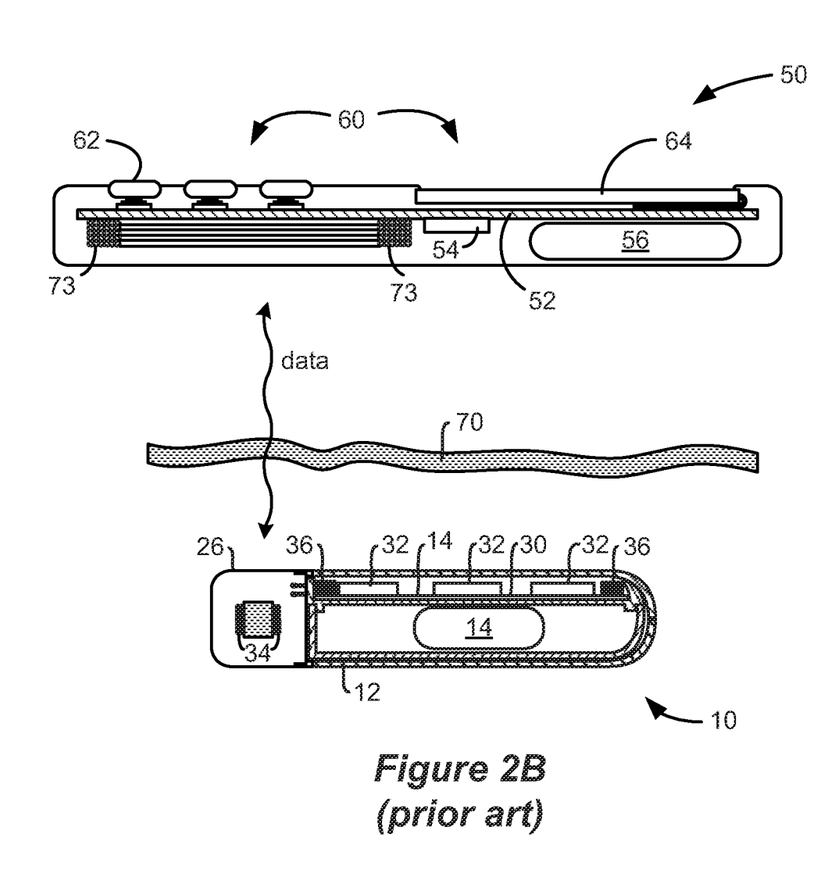

As shown in the cross-section of FIG. 2B, the IPG 10 typically includes an electronic substrate assembly including a printed circuit board (PCB) 30 containing various electronic components 32. Two coils (more generally, antennas) are generally present in the IPG 10: a telemetry coil 34 for transmitting/receiving data to/from an external controller 50; and a charging coil 36 for charging or recharging the IPG's battery 14 using an external charger (not shown). (FIG. 1B shows the IPG 10 with the case 12 removed to ease the viewing of the two coils 34 and 36).

FIG. 2A shows a plan view of the external controller 50, and FIG. 2B shows the external controller 50 in relation to the IPG 100 with which it communicates. The external controller 50 is shown as a traditional hand-held patient controller, although it could also comprise a clinician programmer of the type typically used in a clinician's office. (A clinician external controller would look differently, as one skilled in the art understands, and typically comprises computer). The external controller 50 is used to send data to and receive data from the IPG 10. For example, the external controller 50 can send programming data such as therapy settings to the IPG 10 to dictate the therapy the IPG 10 will provide to the patient. Also, the external controller 50 can act as a receiver of data from the IPG 10, such as various data reporting on the IPG's status.

As shown in FIG. 2B, the external controller 50, like the IPG 100, also contains a PCB 52 on which electronic components 54 are placed to control operation of the external controller 50. The external controller 50 is powered by a battery 56, but could also be powered by plugging it into a wall outlet for example.

The external controller 50 typically comprises a user interface 60 similar to that used for a portable computer, cell phone, or other hand held electronic device. The user interface 60 typically comprises touchable buttons 62 and a display 64, which allows the patient or clinician to send therapy programs to the IPG 10, and to review any relevant status information reported from the IPG 10.

Wireless data transfer between the IPG 10 and the external controller 50 preferably takes place via inductive coupling. This typically occurs using a well-known Frequency Shift Keying (FSK) protocol, in which logic '0' bits are modulated at a first frequency (e.g., 121 kHz), and logic '1' bits are modulated at a second frequency (e.g., 129 kHz). To implement such communications, both the IPG 10 and the external controller 50 have communication coils 34 and 58 respectively. Either coil can act as the transmitter or the receiver, thus allowing for two-way communication between the two devices. This means of communicating by inductive coupling is transcutaneous, meaning it can occur through the patient's tissue 70.

Figure 3:
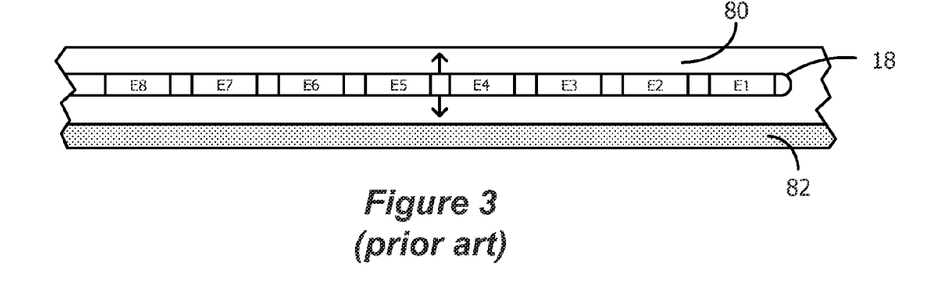
FIGS. 3, 4A, and 4B show an electrode leads positioned in an epidural space within a patient's spinal cord, and shows how the positioning of the lead can change based on a patient's posture.

The lead 18 in an SCS application is typically inserted into the epidural space 80 proximate to the dura 82 within the patient's spinal cord, as illustrated in cross section in FIG. 3. The proximate portion of the lead 18 is tunneled through the patient where it is attached to the lead connector 24 of the IPG 10, which is implanted a somewhat distant location from the lead, such as in the upper portion of the patient's buttocks. Typically in an SCS application, there are two leads implanted in the left and right sides of the spinal column, so that stimulation therapy can be delivered by the IPG 10 to left- and right-branching nerves from the dura 82. However, only one such lead is shown in FIG. 3 for simplicity.

Once implanted, the patient is typically put though a fitting procedure to determine effective therapy to treat the patient's symptoms. This typically occurs in a clinician's office, and may be somewhat experimental in nature. (Some aspects of fitting may also occur prior to full implantation of the IPG 10 during an external trial stimulation phase, which is discussed in U.S. Patent Publication 2010/0228324 for example).

Generally speaking, during the fitting procedure, various stimulation parameters are applied by the IPG 10 to determine what feels best for the patient, and then such stimulation parameters can then be stored in the IPG 10 as a stimulation program. Stimulation parameters can include which electrodes 16 on the lead 18 are active, the polarity of the active electrodes (i.e., whether they act as anodes (current sources) or cathodes (current sinks)), the magnitude of the current pulses applied at the active electrodes (which may comprise either a voltage or current magnitude), the duration of the pulses, the frequency of the pulses, and other parameters. These stimulation parameters can be varied by the external controller 50—either a clinician programmer or a hand-held patient controller—which wirelessly communicates with the telemetry coil 34 in the IPG 10 to change and store the parameters in the IPG 10. After a stimulation program has been set by the clinician, and the patient has left the clinician's office, the patient can modify the stimulation parameters of that program using his hand-held patient controller.

The art has recognized that patients may benefit from the use of different stimulation at different times, and in particular depending on the patient's posture or activity. This is because the position of the lead 18 may move in the epidural space 50 as the patient changes moves, e.g., from supine (on one's back), to standing, to prone (on one's stomach). This is shown by the arrows in FIG. 3. As seen, as the patient moves, the distance between the electrodes 16 and the dura 82 can change. This change in distance can warrant changes in therapy.

In the prior art, such changes in patient posture or activity were sensed by an accelerometer in the IPG 10. As is well known, an accelerometer can detect its position in three-dimensional (3D) space by assessing gravitational forces, and so can detect the 3D position of a patient in which it is implanted. According to this technique, a patient is somewhat relieved of the obligation to manually adjust his stimulation parameters when changing postures, because the IPG can recognize a change in body posture and remember the level of stimulation needed. Thus, in the prior art, an IPG 100 could sense when the patient changes posture; learn from previous experience and remember the patient's last comfortable setting for that posture; and respond by automatically adjusting stimulation to the patient's chosen setting for that posture.

DETAILED DESCRIPTION

The inventors see shortcomings from the prior-art-based method of using an accelerometer in an IPG to sense patient posture and thus to determine an appropriate stimulation program for the patient. For one, the prior art does not consider that forces other than accelerative (e.g., gravitational) forces might be impingent upon the patient in a manner indicative of posture and thus affecting therapy. This can lead to misleading assumptions about the patient's posture. For example, an accelerometer in an IPG might conclude that a patient lying prone and a patient standing but bending forward are in the same posture, when reality is otherwise. Likewise, an accelerometer might conclude that a patient standing up and a patient sitting down are in the same posture, again when this is not true.

Figure 4A:
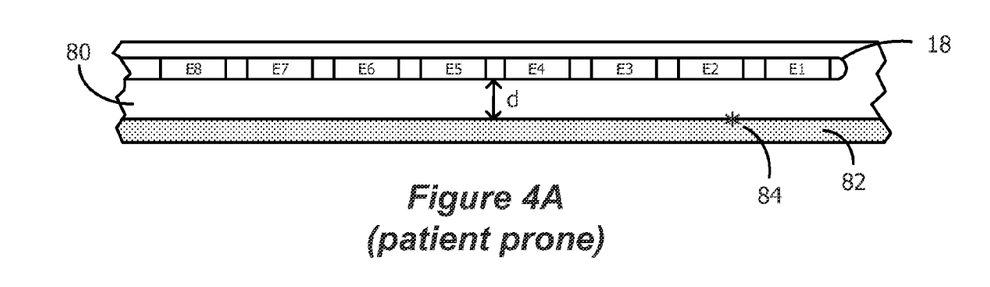

The inventors see such distinctions as significant, particularly upon realizing that the positioning of electrodes on the lead 18 can vary relative to the dura 82 in unpredictable and non-uniform ways. Consider FIGS. 4A and 4B. In FIG. 4A, it is assumed that the patient is lying prone, with the result that the lead 18 has generally moved away from the dura 82 by a constant distance, d, along its entire length. By contrast, in FIG. 4B, it is assumed the patient is standing but bending forward. When the patient bends in this manner, the epidural space 80 and dura 82 will also bend while the lead 18 remains relatively straight, with the result that the distance between the electrodes and the dura 80 is not constant, with some electrodes closer and some farther away. Additionally, when the patient bends, the lead 18 can also shift laterally in the epidural space 80, as shown by the arrow in FIG. 4B. This too changes the positioning of the electrodes relative to the dura 50. For example, consider a nerve branch 84 that causes pain for a patient and requires neurostimulation. In FIG. 4A, activation of electrode E2 would be most likely to recruit and treat nerve branch 84. However lateral shifting of the lead in FIG. 4B now brings electrode E1 closer to nerve branch 84, suggesting that activation of that electrode, rather than E2, would provide the best therapy for the patient.

Figure 4B:
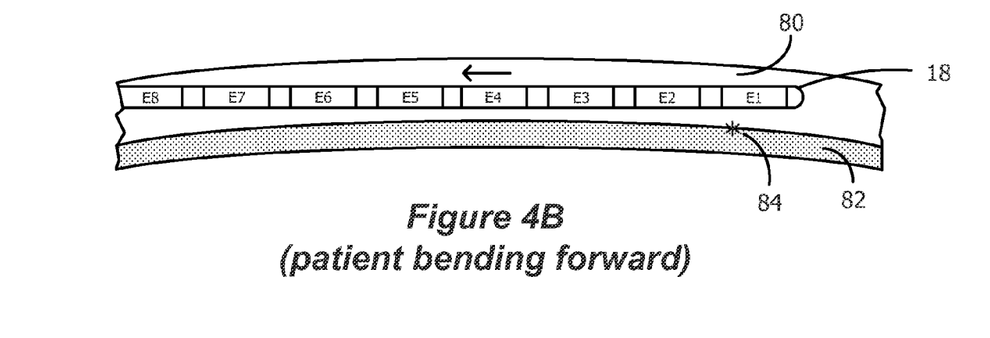

Despite these postural differences, an accelerometer based approach might determine that both of the patient postures in FIGS. 4A and 4B are the same, and therefore might conclude that a single stimulation program is appropriate for both postures, when in reality, different stimulation programs for each posture may be beneficial.

In recognition of this fact, the inventors approach to determining patient posture, and hence what stimulation program is effective, relies on measurements taken at the electrodes. Specifically, and as will be discussed in further detail below, impedance measurements of the patient's tissue are taken at the electrodes, which measurements can comprise complex impedance measurements (magnitude and phase) taken at different frequencies. Such impedance measurements, which can be taken interleaved with stimulation therapy, are used to determine an "impedance fingerprint." This fingerprint can be compared to other known fingerprints stored in the IPG, which known fingerprints are associated with particular stimulation programs. When a measured fingerprint matches one stored in the IPG, the stimulation program associated with the stored fingerprint is automatically selected for patient therapy. If the stimulation program is changed for a given posture, such changes will be stored with its associated fingerprint to remember these changes for the next time the patient is in the relevant posture. Additionally, as new fingerprints are measured which do not match those stored, the IPG can learn and store a new stimulation program for such new fingerprint by remembering stimulation parameters selected by the patient when such fingerprint is encountered. As such, the IPG can learn new postures and new stimulation programs "on the fly" as simulation is occurring, and as the patient goes about his day.

Figure 5:
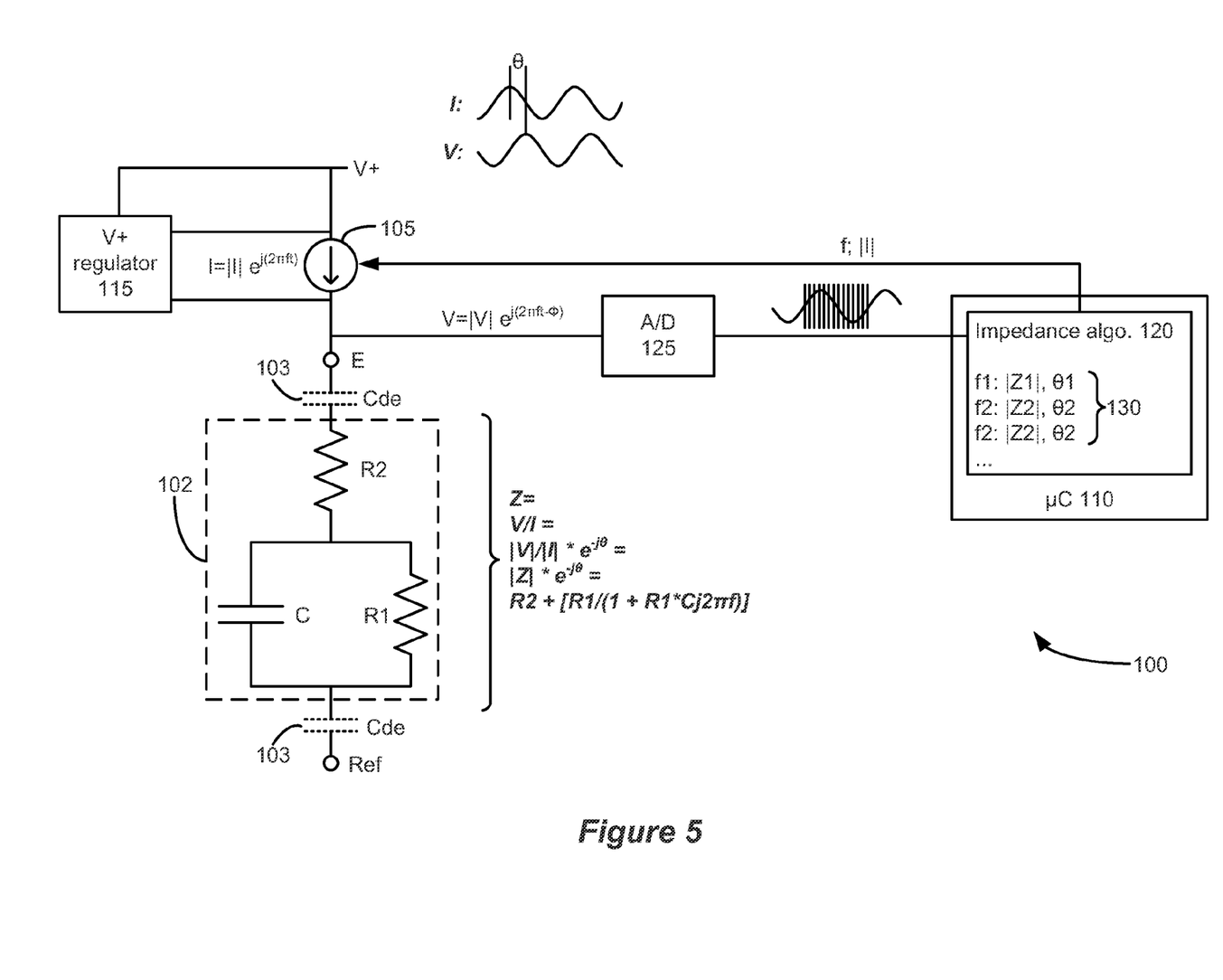
FIG. 5 shows an illustration of impedance monitoring circuitry in accordance with an embodiment of the invention for measuring an impedance between two electrodes of an IPG, including an impedance algorithm.

Before discussing particulars of the technique, an example of impedance monitoring circuitry 100 useable in an IPG 10 in accordance with the technique is disclosed in FIG. 5. For simplicity, the circuitry 100 is shown for only a single electrode E, but such circuitry would in an actual implementation be duplicated or shared so that the impedance at all electrodes can be monitored. The depicted impedance monitoring circuitry is but one example of circuitry capable of performing impedance measurements, and should not be taken in a limiting sense.

Electrode E is shown relative to another reference electrode, Ref, which (as will be discussed subsequently) could comprise another electrode on the lead 18 or the IPG's conductive case 12 (FIG. 1A). A patient's tissue intervening between the electrode and the reference is modeled 102 as an R-C network, with a capacitor C and resistor R1 in parallel, and that parallel combination coupled to a series resistor R2. Generally speaking, tissue fluids are modeled by R2, while cell membranes in the tissue are modeled by the parallel connection of C and R1. Tissue model 102 could be further refined, with different resistances and capacitances to better fit the reality of the environment of the tissue, but the simple three component model 102 serves for purpose of illustration. By virtue of the capacitance, the impedance Z of the tissue will be complex, as shown by the equations in FIG. 5. As such, the AC voltage V produced across the tissue in response to a constant AC current through the tissue will be phased-shifted (A) relative to the current, as shown in the waveforms.

In one example, the measurement signal for the impedance measurement is provided by a AC constant current source 105. The magnitude, |I|, and frequency, f, of the produced current is controlled by an impedance algorithm 120 operating in a microcontroller 110, which algorithm will be discussed in further detail below. Microcontroller 110 can comprise any known central processor or controller typically present in an IPG 100, or any logic circuitry more generally. The voltage drop across the current source can be monitored by a compliance voltage regulator 115, which is used to generate a compliance voltage V+ sufficient to provide the desired current I without loading, and in an efficient manner considerate of power draw from the IPG's battery 14. Suitable compliance voltage regulation circuitry 115 can be found in U.S. Patent Application Ser. No. 61/654,606, filed Jun. 1, 2012, which is incorporated by reference, and with which the reader is assumed familiar. Typically, the magnitude of the constant current |I| used for the impedance measurement will be much lower than typical magnitudes used for therapeutic currents, and hence won't be noticed by the patient. For example, |I| can range from 1 microamp to 100 microamps. Current source 105, depending on its complexity, can also be used to generate the therapeutic stimulation pulses to the patient (see FIG. 10), or may be separate from the sources used to generate the stimulation pulses.

Monitoring of tissue impedance occurs under the control of the impedance algorithm 120 operating in the microcontroller 110, which algorithm, as will be discussed further later, can operate while the IPG 10 is providing stimulation to the patient. At an appropriate time for a measurement, the impedance algorithm 120 sends the magnitude, |I|, and frequency, f, of the measuring signal I to the current source 105. The resulting AC voltage V at electrode E resulting in response to the measurement signal I is then digitized at an Analog-to-Digital (A/D) converter 125, which samples the voltage at an appropriate rate (such as every ten degrees) and an appropriate number of times (such as over 180 degrees) to allow the impedance algorithm 120 to discern the waveform's magnitude, |V|, and phase, θ, relative to the current. (It is assumed here that the impedance algorithm 120 understands the relative phase θ between the voltage and the current by virtue of its control of the current source 105. However, if necessary, the phase of the current I can also be monitored, and compared with the voltage at a phase detector, to provide the relative phase θ to the impedance algorithm).

Once the voltage magnitude, |V|, and phase, θ, have been determined by the impedance algorithm 75, the complex impedance, Z, of the tissue can be calculated based upon the impedance algorithm 75's a priori knowledge of the current magnitude, |I|. Specifically, and as shown in the equations in FIG. 5:

$$Z=V/I=|V|/|I|*e^{-j\theta}=|Z|*e^{-j\theta}$$

where the magnitude of the impedance, |Z|, comprises the ratio between the magnitudes of the voltage and the current (i.e., |Z|=|V|/|I|). The magnitude, |Z|, and phase, θ, of this impedance 130 are stored by the impedance algorithm 120 a given frequency. Such storage may be within memory in the microcontroller 110, or a separate memory associated with and controlled by the microcontroller. In a preferred embodiment, the impedance measurement 130 can be repeated at electrode E at other frequencies, thus allowing new magnitudes, |Z|, and phases, θ, to be determined and stored, as discussed further below.

Figure 6:
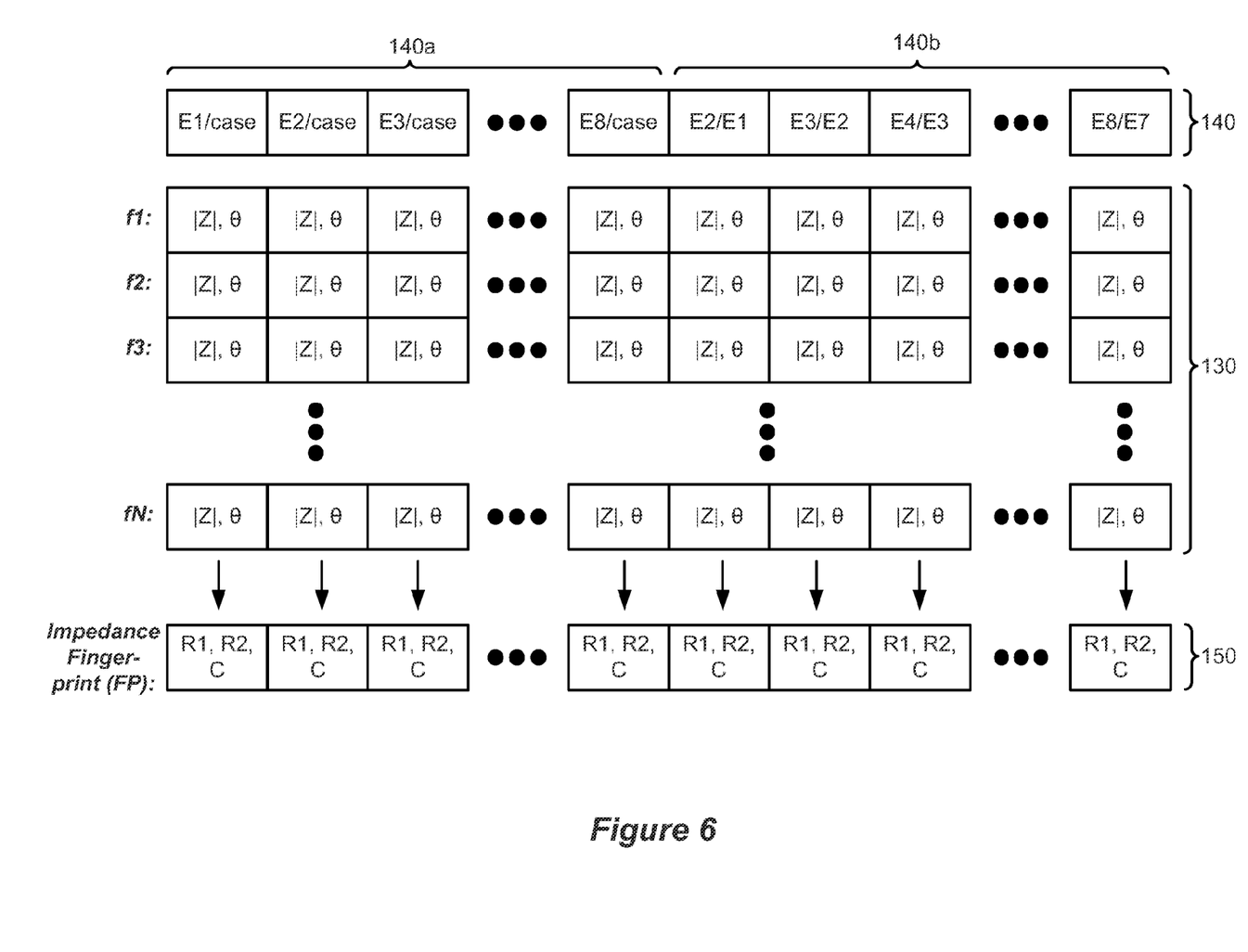
FIG. 6 shows how the impedance algorithm can compile the impedance measurements into an impedance fingerprint indicative of the tissue impedance between various electrode combinations.

FIG. 6 illustrates how such impedance measurements 130 can be compiled and processed by the impedance algorithm 120 to determine an impedance fingerprint 150 of the tissue. Different electrodes may act as the reference electrode (Ref; FIG. 5) for any particular electrode whose impedance is being measured. For example, in electrode combinations 140a, the conductive case 12 acts as the reference electrode (e.g., ground) relative to each of the measured electrodes. This is desirable to understand each electrode's impedance relative to something akin to a system ground, which a large case electrode essentially provides in the relatively conductive environment of a patient's tissue.

In electrode combinations 140b, the impedance at each electrode is measured relative to its neighbor: E2 to E1, E3 to E2, etc., and so such neighbor acts as the reference. This is desirable because the electrodes can have different distances to relevant structures. For example, and referring again to FIG. 4B in which the tissue is bent relative to the lead 18, if the impedances of the epidural space 80 and the dura 82 differ, then it would be expected that the impedance between E4 and E3 (which are relatively close to the dura 82) and electrodes E8 and E7 (which are relatively far from the dura), would be significantly different. In short, the combined information provided by electrode combinations 140a and 140b should provide a reliable assessment of the tissue impedance relative to the electrodes. However, other electrode combinations are possible, and greater numbers of electrode combination impedance measurements will increase the resolution of the resulting fingerprint, and thus increase the likelihood of eventually automatically choosing an appropriate stimulation program based on postural changes. Moreover, an electrode combination 140 may also include more than simply a pair of two electrodes, and can instead comprise an impedance measurement taken between a more-complex tissue network defined by three or more electrodes.

Taking measurements at different frequencies allows the impedance algorithm 120 to compute values for the various components between the two electrodes in the tissue model 102—R1, R2, and C—to be determined. Because tissue model 102 contains three unknown values, measurements are taken at least three frequencies, thus rendering a system of equations from which the impedance algorithm 120 can deduce R1, R2, and C between a given electrode combination 140.

Figure 7:
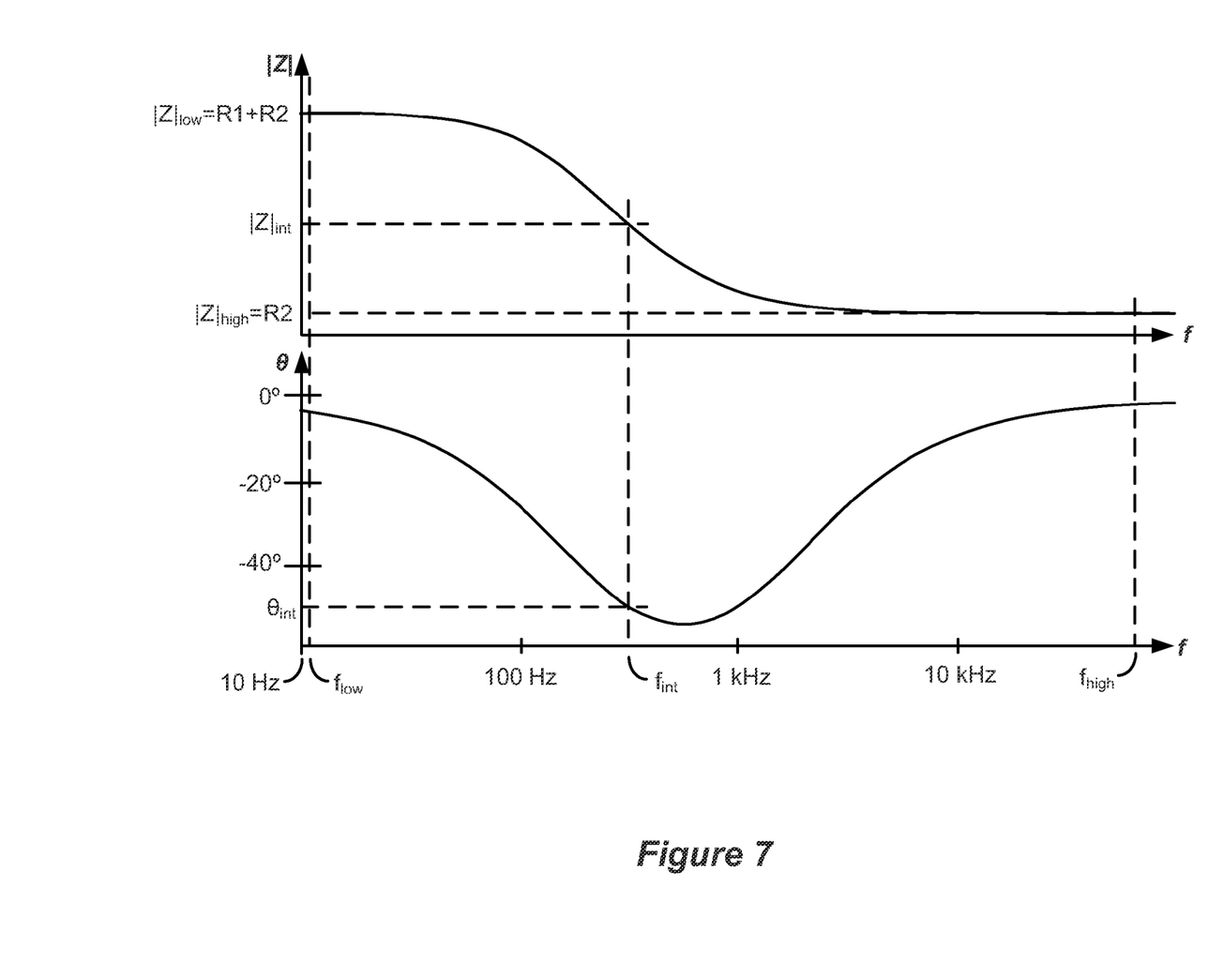
FIG. 7 shows an example of how the impedance measurements in FIG. 6 for a given electrode combination can be taken at more than one frequency.

FIG. 7 shows a simple example of three such measurements, taken at low intermediate, and high frequencies ($f_{low}$, $f_{int}$, and $f_{high}$), and assuming that no decoupling capacitors 103 (FIG. 5) are included in the measurement. (Decoupling capacitors 103 are discussed further below). The simulation assumes that R2=100 ohms, R1=900 ohms, and C=1 µF, although experimentation may be required to determine values that are more indicative of a patient's actual tissue. If the frequency of $f_{low}$ is small enough (e.g., tens of Hertz), the capacitor C can be assumed to be an open circuit in the tissue model 102, meaning the measured impedance magnitude ($|Z|_{low}$) is dominated by the sum of R1 and R2. Likewise, if the frequency of $f_{high}$ is high enough (e.g., tens of kilohertz), the capacitor C can be assumed to be a short circuit, meaning the measured impedance magnitude ($|Z|_{high}$) is dominated by R2 alone. In other words, the values for R1 and R2 can be determined, or at least estimated, solely using the impedance magnitudes at these two frequencies. A third impedance measurement, $f_{int}$, is taken at some intermediate frequency, which may be one which experimentation teaches results in an impedance magnitude that is about half of the maximum magnitude expected (e.g., ½(R1+R2)). This third measurement renders an impedance of $|Z|_{int}$ and $\theta_{int}$, which can then be used to determine the value of the capacitor C. Specifically, and using the equations set forth in FIG. 5:

$$|Z|_{int}*e^{-j\theta int}=R2+(R1/(1+R1*Cj2\pi f_{int}))$$

which can be solved for C. However, this simple method, whereby R1 and R2 are determined by making simple assumptions about the capacitance, is not strictly necessary. Measurements at any three frequencies can be used, rendering a system of equations from which R1, R2, and C can be solved from ($|Z|1$, $\theta 1$, f1), ($|Z|2$, $\theta 2$, f2) and ($|Z|3$, $\theta 3$, f3).

While the particular tissue model 102 here assumes three unknown values, other more or less complex tissue models 102 could exist, warranting different numbers of minimal frequency measurements to allow for the values in such models to be solved. Inclusion of measurements at more than a minimal number of frequencies allows the unknown tissue model values to be determined with increased reliability. In one example, the impedance measurements can be taken over frequencies ranging from about 20 Hz to 50 kHz.

It is known in the art of implantable neurostimulators to connect decoupling capacitors 103 (FIG. 5) to stimulating electrodes to prevent the direct injection of DC current into a patient tissue, which can be a safety concern. If present, such decoupling capacitors 103 may be included in the impedance measurement, yielding a total measured impedance of $$|Z|*e^{-j\Theta}=(2/C_{de}j2\pi f)+R2+(R1/(1+R1*Cj2\pi f))$$

where ($2/C_{de}j2\pi f$) comprises the series impedance of the two decoupling capacitors 103. Because the capacitances of the decoupling capacitors, Cde, are known, they will not affect the ability to discern the unknown tissue values of R1, R2, and C by measuring at three different frequencies. (Note however that the inclusion of the decoupling capacitors 103 in the impedance measurement does not allow for the simple approximation of R1 and R2 at high and low frequencies, as shown in FIG. 7).

Referring again to FIG. 6, once the impedance algorithm 120 has computed the tissue model values (R1, R2, and C) for each of the electrode combinations 140, these values taken together comprise an impedance fingerprint (FP) 150. While it is informative that the fingerprint 150 comprises the solved-for values of electrical components in the tissue model 102, this is not strictly necessary. Instead, the fingerprint 150 can be comprised of any other suitable metric or metrics indicative of the complex impedance of the various electrode combinations 140. For example, the portion of the impedance fingerprint 150 for any given electrode combination 140 can comprise the raw impedance magnitudes and phases ($|Z|$, $\theta$) measured at the various frequencies, or some other processing of this raw information short of solving tissue model values. Indeed, because it is not strictly necessary to solve tissue model values, it is not strictly necessary that the fingerprint 150 comprise information taken at any particular number of frequencies. Experience may teach that complex impedances measured at a single frequency may be sufficient to reliably discern patient posture. Additionally, the impedance fingerprint 150 may involve processing the impedance measurements or tissue model values for each of the electrode combinations together into a new metric.

Figure 8:
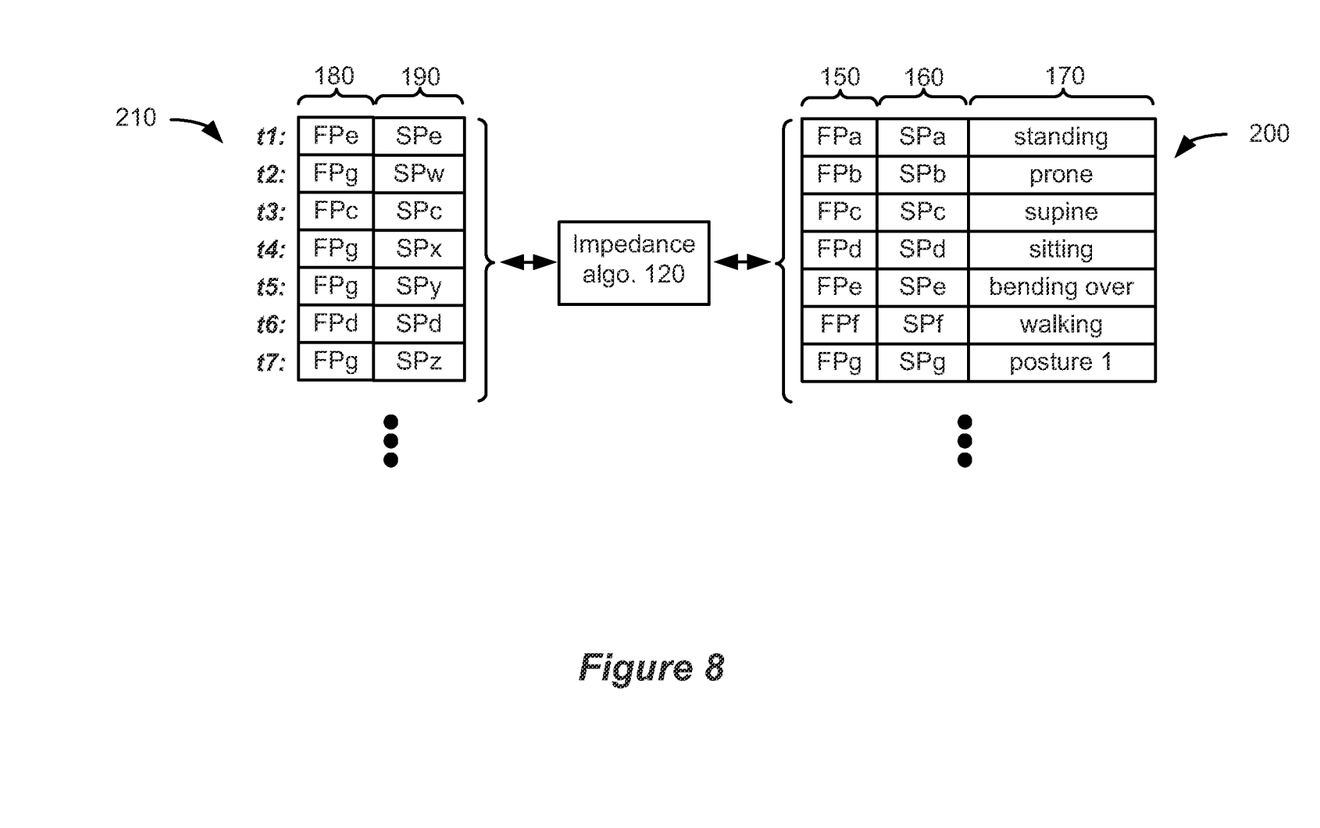
FIG. 8 shows how the impedance algorithm interfaces with a fingerprint database comprising known impedance fingerprints and associated stimulation programs indicative of a patient posture, and interfaces with a fingerprint log comprising measured fingerprints.

The impedance fingerprint 150 is stored by the impedance algorithm 120 in a fingerprint database 200, as shown in FIG. 8. The fingerprint database 200, like the impedance measurements 130, can be stored in any suitable memory in the IPG 10. The fingerprints 150 in the database 200 are each associated with a stimulation program (SP) 160, which may be determined during a fitting procedure with a clinician, or which may be new fingerprints learned on the fly, as discussed below.

Stimulation programs SPa-SPf are assumed in the illustrated example of FIG. 8 to be determined during a fitting procedure. For example, the clinician will ask the patient to stand, and then instruct the IPG 100 using an external controller 50 to take and store an impedance fingerprint 150 (FPa). While still standing, the clinician will adjust the stimulation parameters using the external controller 50—which again may comprise one of more of which electrodes are active, the polarity of the active electrodes, the magnitude, duration, and frequency of the current pulses applied at the active electrodes, or other parameters—to determine a stimulation program 160 that provides desirable therapy for the patient in the standing position (SPa). The fingerprint (FPa) and stimulation program (SPa) are then associated in the fingerprint database 200. Thereafter, the clinician will have the patient take new postures, and repeat the above procedure to determine various fingerprints (FPx) and stimulation programs (SPx) and store and associate them in the fingerprint database 200.

It is not strictly necessary that the fingerprint database 200 be pre-populated with posture related fingerprints 150 and associated stimulation programs 160 during a fitting procedure, as the system can learn and store new fingerprints and stimulation programs on the fly, as discussed further below. Both learned fingerprints and fingerprints determined during a fitting session are said to be pre-determined once stored in the database 200.

It should be noted that the fingerprints 150 stored in fingerprint database 200 may from time to time require updating. Such updating is useful when it is recognized that the physiology around the IPG 10 and lead 18 can change over the course of its useful life. For example, scar tissue may develop around the electrodes 16 on lead 18 or the case 12, or the lead 18 may over time settle into a particular position in the epidural space 80, either of which may require altering of the fingerprints 150 in the database 200. As such, it should be understood that the fingerprints 150 in database 200 will from time to time be updated, either in a clinician's office as described above, or under the control of the patient. For example, the microcontroller 110 in the IPG 10 can be controlled to communicate to the external controller 50 when it is reasonable to update the various fingerprints stored in the database 200, perhaps every six months or so. When the patient is so notified by the external controller 50, the user interface 60 of the external programmer 50 can be programmed to walk the patient through a fitting procedure similar to that described above, allowing new impedance measurements to be taken in the different postures understood by the database 200, and to update the stored fingerprints 150 associated with these postures. However, and again, such periodic re-fitting and pre-population of the fingerprint database 200 is not strictly necessary if fingerprints are learned and stored in the database 200 on the fly, as discussed further below.

Figure 9A:
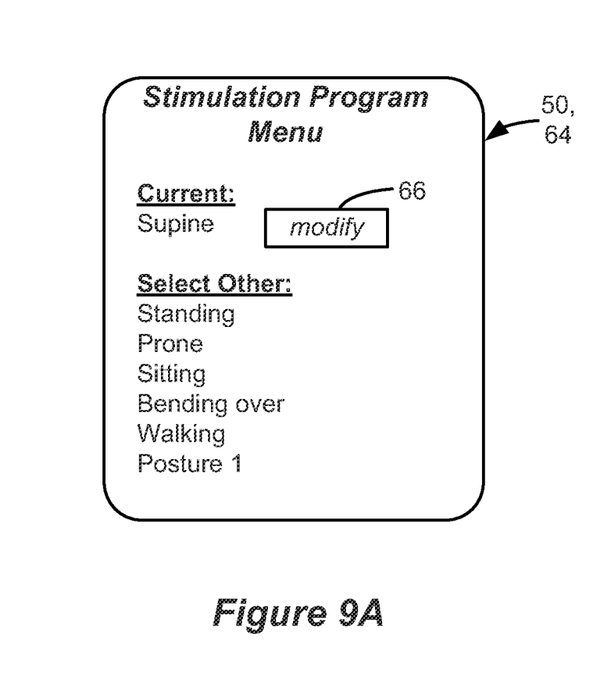
FIGS. 9A and 9B show a display of an external controller in communication with an IPG comprising the impedance monitoring circuitry, and show how a user can review and rename postures identified by the IPG, and modify the stimulation program associated with an identified posture.

The database 200 may optionally store a textual description 170 of the posture, which again may be entered into the external controller 50 by the clinician during the fitting procedure. This can be useful to allow the external controller 50 to query the various postures stored in the fingerprint database 200. For example, by communicating the textual description 170 of the currently-running stimulation program 160 to the external controller 50, the patient can verify that that program matches the patient's actual posture. Displaying a textual description 170 of the posture at the external controller 50 is also useful to allow the patient to modify that stimulation program, or to select a different stimulation program, as shown in example display 64 of the external controller 50 in FIG. 9A. In a preferred embodiment, if the patient manipulates user interface 60 of the external controller 50 to modify any of the simulation parameters for a stimulation program 160 currently operating in the IPG 10, as identified by user selection 66, the stimulation program 160 in the fingerprint database 200 will be automatically updated with the new parameters so that these new parameters will be applied when the IPG 10 senses the fingerprint 150 associated with that stimulation program 160. This allows the IPG 10 to learn new parameters for the stimulation programs based on patient feedback.

Once the fingerprint database 200 has been populated or updated in this manner, the impedance algorithm 120 need merely take fingerprint measurements from time to time, match them to those stored in the database 200 if possible, and choose the associated stimulation program 160 from the database 200 to provide patient therapy. In this regard, and as shown in FIG. 8, measured fingerprints 180 can be stored in a fingerprint log 210 associated with a timestamp, and (optionally) the stimulation program 190 running at that time. Log 210 as before can be stored in any suitable memory in the IPG 10. Although only strictly necessary to the disclosed technique to store the currently-measured fingerprint 180, storing a time-stamped history of fingerprints in the log 210 will allow the impedance algorithm 120 to perhaps identify new postures currently unknown to the database 200, as explained further below. The log 210 may be limited in its capacity to store only a reasonable number of fingerprint measurements 180, for example, those occurring over the course of a day.

At a given time (e.g., t3), the impedance algorithm 120 determines the currently-measured fingerprint 180 in the log 210 (e.g., FPc). If the impedance algorithm 120 can match this measured fingerprint 180 to a fingerprint 150 stored in the database 200 (e.g., FPc), the impedance algorithm 120 will cause stimulation program SPc associated with FPc in the database 200 to be applied to the patient. If the impedance algorithm 120 cannot match the measured fingerprint 180 to a fingerprint 150 in the database 200, the impedance algorithm 120 may take no action with regard to modifying the therapy currently being applied to the patient. Or, the unrecognized measured fingerprint 180, once learned on the fly, can be stored in the database 200 and associated with an appropriate stimulation program, as described in the next paragraph. One skilled in the art will understand that matching the measured fingerprints 180 in log 210 with the stored fingerprints 150 in database 200 may require a comparison that is acceptable within some margin of error, as it cannot be expected that any given measured fingerprint 180 will exactly match one stored in the database 200. For example, it may be sufficient that all values (R1, R2, C) in the two fingerprints 180 and 150 match within 20%, or that 85% of them match within 10%, or such other statistical metrics that may be suitable based upon routine experimentation and empirical data.

Other postures in the fingerprint database 200, such as "posture 1," may presently be unknown, but may be determined based on new impedance fingerprints that the IPG 100 learns on the fly. The fingerprint log 210 previously discussed is useful in this regard. The impedance algorithm 120 can from time to time check the fingerprint measurements 180 in the log 210 to see if a particular fingerprint is occurring with relevant frequency. For example, suppose a particular patient likes to sleep on his right side—a posture that was not addressed during the fitting procedure. The impedance algorithm 120 may notice a measured fingerprint 180 (e.g., FPg) associated with this posture in log 210 that occurs frequently, but is unknown to the impedance algorithm 120 because it doesn't match with any of the fingerprints 150 stored in the database 200. When assessing measured fingerprints 180 to determine the frequency of their occurrence, it cannot be assumed that any two (or more) measured fingerprints 180 in log 210 will match exactly, and again the impedance algorithm 120 may need to employ statistical metrics to make this determination.

When a predictable but unknown fingerprint (e.g., FPg) is present in log 210, the impedance algorithm 120 may determine a new posture, and can add this new fingerprint (perhaps as averaged where it variously occurs in log 180) to the database 200. If this measured fingerprint 180 is associated with stimulation program(s) 190 in the log 210, which stimulation programs may have resulted from patient changes, some indication of the associated stimulation program(s) 190 can be stored in the database 200 as well.

For example, if the stimulation programs associated with FPg are not uniform in the log 210 (e.g., SPw-SPz), the impedance algorithm 120 can average them in some manner to determine and store a singular stimulation program (SPg) with FPg in the database 200. Or, the impedance algorithm 120 may simply store the last stimulation program in the log 210 associated with FPg in the database 200 (e.g., SPz, which may simply default to the preceding stimulation program SPd). If review of the log 210 results in no important information relevant to stimulation associated with the new fingerprint—for example, if SPw-z do not indicate some change by the patient beyond the last stimulation program that was applied when the new fingerprint was encountered—then SPg can simply be associated with default or currently-pending stimulation parameters in the database 200. Once entered in the database 200, the stimulation program SPg associated with new fingerprint FPg can be updated based on the patient's modification of the stimulation parameters while in such posture, i.e., while FPg is currently being applied by the IPG 10, as explained earlier.

Thereafter, once new fingerprint FPg is recognized and learned by the impedance algorithm 120 in the log 210 and stored in database 200, the IPG 10 can automatically switch therapy to its associated program (SPg) in the database 200 when this now pre-determined fingerprint is encountered, even though the IPG 10 has no a priori understanding of the patient's posture based upon fitting. If textual descriptions 170 of posture are provided in the database 200, the IPG 10 may assign a generic textual description to such new and unidentified posture (i.e., "posture 1").

Figure 9B:
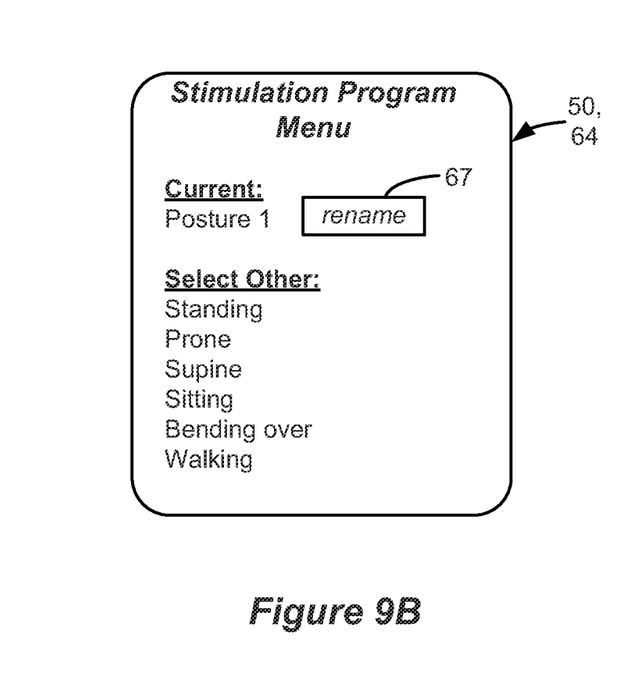

At some point in future, the IPG 10 can attempt to communicate with the external controller 50 to inform the patient that a new posture has been identified, and allow the patient to name this new posture. This is shown in FIG. 9B. As shown, the display 64 of the external controller 50 identifies that the current posture of the patient is generically described as "posture 1," and allows the patient to rename the description of this posture to something meaningful to the patient per user selection 67, for example "right side." If this textual description is updated by the patient, the external controller 50 would telemeter this new textual description 170 to database 200 to overwrite the "posture 1" placeholder provisionally assigned in the database 200 for the relevant stored fingerprint 150 (FPg). If the patient does not choose to update the textual description per selection 67, there is no consequence to patient therapy: the impedance algorithm 120 can still change the stimulation program based on its detection of fingerprint FPg, including any patient modifications captured within stimulation program 160 with which it is associated.

The above example by which an unknown fingerprint FPg is determined and ultimately associated with a stimulation program SPg in the fingerprint database 200 illustrates that the fitting procedure described earlier is not strictly necessary—that is, it is not necessary to pre-populate the database 200 with fingerprint taken at known postures and associated stimulation programs taken at known patient postures. Just as sleeping on the patient's right side was initially unknown to the IPG 10, all of the postures represented in FIG. 8 may be unknown but eventually discovered. For example, the impedance algorithm may notice that a fingerprint associated with a standing patient occurs frequently (FPa), and over time—and based on patient adjustment of the stimulation parameters while in that posture—can eventually learn and store the stimulation program (SPa) to associate with that fingerprint in the database 200. Thus, the impedance algorithm 120 can entirely self-populate the fingerprint database 200 thus allowing the IPG 10 to learn which stimulation programs best suit the patient for a given measured impedance fingerprint.

Even if physiological changes (scarring) eventually cause changes to the learned fingerprints, such changes can be tracked and updated automatically. For example, an initial fingerprint FPa associated with a standing position may over time change, in which case the impedance algorithm 120 will recognize the change, and may eventually determine a new fingerprint (e.g., FPh) for this position, which is stored in the fingerprint database 200 and associated with its stimulation program (e.g., SPh). The earlier fingerprint FPa for this position may thus over time become moot, in which case it will never match the currently-measured fingerprints, and hence its associated stimulation program SPa will never be chosen by the impedance algorithm 120 for patient therapy. In this regard, the impedance algorithm 120 can monitor how often fingerprints in the database 200 are matched with those currently being measured, and if particular fingerprints have not been matched for some time, the impedance algorithm may eventually delete such now-moot fingerprints and their associated stimulation programs from the database 200.

The disclosed technique is further beneficial because its reliance on electrical measurements means that therapy can be adjusted as a result of any factor affecting electrode impedance, whether based upon the patient's posture or not. In this regard, "posture" should be understood as including anything that can affect the positioning or impedance of electrodes in the patient, including static postures, active postures (such as walking or running), gravity, accelerative forces, etc.

Figure 10A:
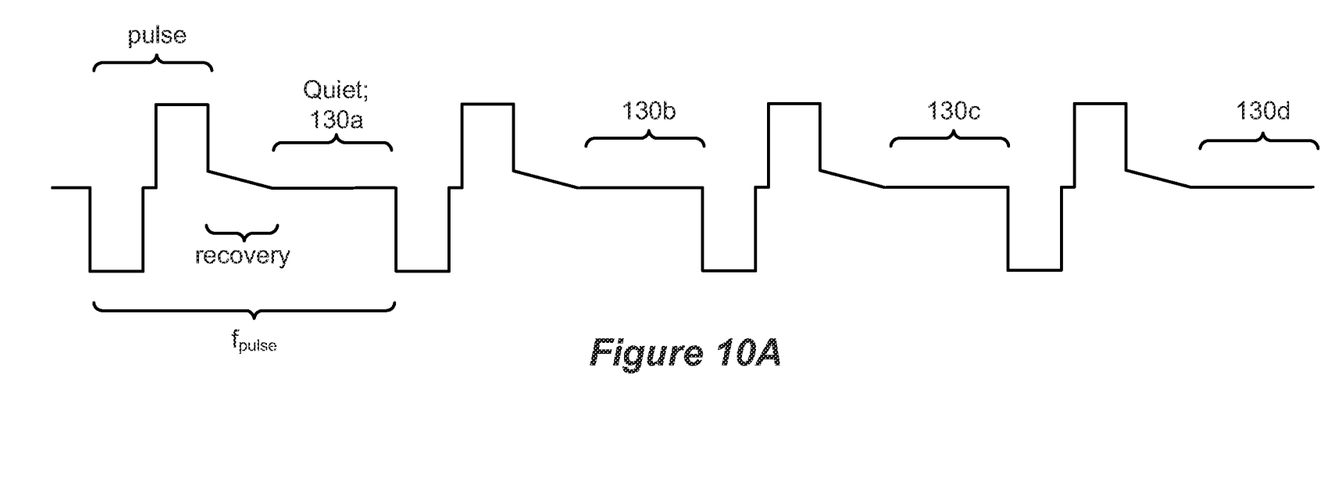
FIGS. 10A and 10B show how and when the impedance measurements comprising an impedance fingerprint can be taken during operation of a stimulation program.
Figure 10B:
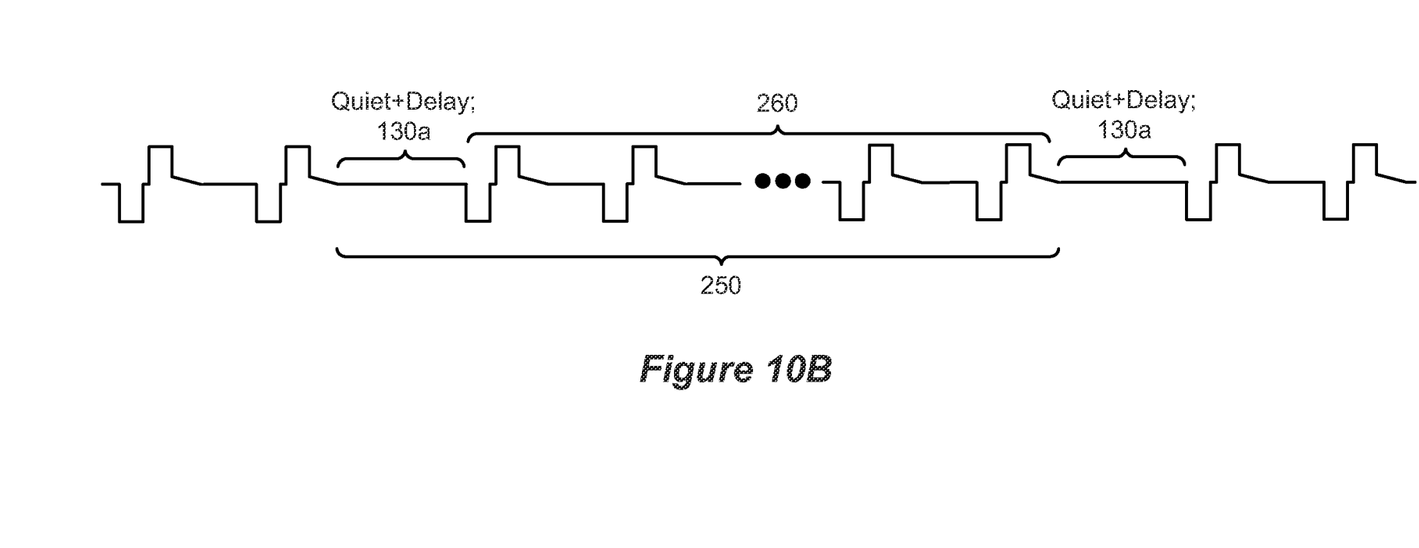

The tissue impedance measurements 130 (FIG. 6) upon which the disclosed technique are based are preferably taken during the provision of a stimulation program to the patient, and FIGS. 10A and 10B shows various ways in which this can occur. Shown are the current pulses being applied to a particular electrode, which comprises an active electrode in the stimulation program currently operating. One skilled will realize that some other electrode will act as the return path for these current pulses, but this is not shown for simplicity. Also, more than two electrodes may be active to provide a more complex therapy to the patient, but again this is not shown.

The therapeutic stimulation pulses in this example are bi-phasic, meaning that they have portions of opposite polarities. This is common in the neurostimulation art to assist in charge recovery from the tissue. To further assist in such recovery, the pulses are followed by a passive recovery period. Biphasic pulses and recovery periods are explained in further detail in U.S. Provisional Patent Applicant Ser. No. 61/654,603, which with the reader is assumed familiar.

The recovery period is followed by a quiet period where no electrode is providing therapy to the patient. These quiet periods are logical times to take the impedance measurements 130 described earlier, which can occur in different ways. Whether impedance measurements can be taken during the quiet periods without interrupting or delaying the pulses depends on the duration of such quiet periods, which in turn depends on the frequency, $f_{pulse}$, of the pulses, and the duration of the pulses and the recovery periods. Whether impedance measurements can be taken during the quiet periods without interrupting or delaying the pulses also depends on the frequency f at which the impedance measurement is taken. Because a given impedance measurement may requiring sampling the resulting voltage V acorns the tissue for some significant portion of its cycle (e.g., 180 degree as noted earlier), the measurement can be taken without interruption if this 180-degree timeframe can fit within the duration of the quiet period—i.e., if $1/(2f) \leq t_{quiet}$—a condition that is more easily met when the frequency of the impedance measurement is higher. If this condition is met, an impedance measurement 130x for at least one electrode combination 140 can be taken during each quiet period, as shown in FIG. 10A.

In the example discussed earlier in an IPG 10 with eight electrodes, 45 impedance measurements 130 would need to be taken to comprise a full fingerprint 150 for each of the fifteen electrode combinations 140 (eight from each electrode to the case, and seven between nearest neighbors) taken at three frequencies. Such measurements will generally not be difficult to take in a reasonable amount of time for updating the fingerprints 180 in the log 210, which need occur only every minute or longer. For example, for pulses occurring at $f_{pulse}=200$ Hz, the 45 impedance measurements can be taken in less than half a second. Of course, greater number of electrodes, electrode combinations 140, or measurement frequencies would increase this time. Although the fingerprints 180 are measured and stored in the log 210 periodically, such measurements need not occur at consistent intervals of time.

If it is not possible to fit a given impedance measurement into a given quiet period—for example, when measuring impedance at lower frequencies—then some of the pulses may require delay or deletion, as shown in FIG. 10B. As shown, the quiet period has been delayed to accommodate the time needed to take an impedance measurement, which depending on the measurement frequency and other timing consideration of the pulse train, may require simply delaying the issuance of a next pulse slightly, or which may require deleting one or more pulses in the train. Because delaying or deleting pulses impacts patient therapy, impedance measurements may only be taken once during a measurement period 250, which should be long enough to allow many uninterrupted therapy pulses 260 to occur at their specified frequency, $f_{pulse}$. For typical timings, it is not expected that the delay periods in FIG. 10B would be significant enough that the patient would notice any change in therapy. Moreover, for typical timings the measurement period 250 will typically be short enough to make the required numbers of measurements (45) in a reasonable time to update the fingerprint 180 in the log 210 (again, at least every minute or so).

Various changes can be made to the particular implementation details describe herein. For example, a constant AC voltage source could be used in lieu of constant AC current source 105, in which case the resulting current through the tissue would be monitored to determine impedance.

While it was assumed that multiple measurement signals at different frequencies be applied between any two electrodes to determine the component values in the tissue model, this is not strictly necessary. For example, a single measurement signal $I(t)=|I_1|*e^{j2\pi f_1 t}+|I_2|*e^{j2\pi f_2 t}+|I_3|*e^{j2\pi f_3 t}$ could be used that comprises three frequency components, f1, f2, and f3. This would allow the impedance algorithm to determine the complex impedance between any electrode combination, and thus the values of the components in the tissue model between them, using a single measurement signal. In this regard, it is not strictly necessary that the measurement signal be comprised of only the frequencies necessary to determine the complex impedance: any periodic signal from a Fourier transform standpoint providing a suitable number of frequencies will suffice, even if such measurement signal contains other significant frequencies, which may be filtered out if they are unnecessary. Provision of a suitable singular measurement signal comprising the requisite number of frequencies would require a more sophisticated current source 105, but such is within the skill of one in the art.

While, while the disclosed technique is particularly applicable to IPGs used in SCS applications, the technique is not so limited, and can be used with any multi-electrode implantable neurostimulation used in other portions of a patient's body for any purpose. In one additional example, the disclosed technique can be used with well-known Deep Brain Stimulators (DBS) as well.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. An implantable stimulator device, comprising:
a plurality of electrodes configured to provide electrical stimulation to a patient; and
circuitry comprising an impedance algorithm configured to determine an impedance between a plurality of combinations of the electrodes at a plurality of different frequencies during quiet periods when the electrical stimulation at a first frequency is not occurring, and to determine a measured impedance fingerprint from the determined impedances,
wherein the impedance algorithm is further configured to select a stimulation program to be provided to the electrodes in accordance with the measured impedance fingerprint.

2. The device of claim 1, wherein the determined impedances are complex impedances.

3. The device of claim 1, further comprising a database configured to store a plurality of pre-determined impedance fingerprints and a plurality of associated stimulation programs, wherein the measured impedance fingerprint is compared to pre-determined impedance fingerprints to select the stimulation program.

4. The device of claim 3, wherein the plurality of pre-determined impedance fingerprints are stored in the database during a fitting procedure.

5. The device of claim 3, wherein the plurality of pre-determined impedance fingerprints are learned as the electrical stimulation is provided to the patient.

6. The device of claim 1, wherein the selected stimulation program comprises one or more stimulation parameters, including which electrodes are active, a polarity of the active electrodes, a magnitude of the electrical stimulation at the active electrodes, a duration of the electrical stimulation, and a frequency of the electrical stimulation.

7. The device of claim 1, wherein the impedance algorithm provides a measurement signal to the plurality of combinations of the electrodes, and assesses responses to the measurement signals, to determine the impedances between the plurality of combinations of the electrodes.

8. The device of claim 7, wherein the measurement signals comprise AC currents, and the responses comprise AC voltages between the plurality of combinations of the electrodes.

9. The device of claim 1, wherein the measured impedance fingerprint comprises values of electrical components in a tissue model between the plurality of combinations of the electrodes.

10. The device of claim 1, wherein the measured impedance fingerprint is indicative of a posture of the patient.

11. An implantable stimulator device, comprising:
a plurality of electrodes configured to provide electrical stimulation to a patient;
circuitry comprising an impedance algorithm configured to determine an impedance between a plurality of combinations of the electrodes at a plurality of different frequencies during quiet periods when the electrical stimulation at a first frequency is not occurring, and to determine a measured impedance fingerprint from the determined impedances; and
a database configured to store a plurality of pre-determined impedance fingerprints and a plurality of associated stimulation programs,
wherein the impedance algorithm is further configured to match the measured impedance fingerprint with a pre-determined impedance fingerprint in the database, and to select the stimulation program associated with that pre-determined fingerprint to be provided to the electrodes.

12. The device of claim 11, wherein the determined impedances are complex impedances.

13. The device of claim 11, wherein the plurality of pre-determined impedance fingerprints and the plurality of associated stimulation programs are stored in the database during a fitting procedure.

14. The device of claim 11, wherein the plurality of pre-determined impedance fingerprints and the plurality of associated stimulation programs are learned as the electrical stimulation is provided to the patient.

15. The device of claim 11, wherein the selected stimulation program comprises one or more stimulation parameters, including which electrodes are active, a polarity of the active electrodes, a magnitude of the electrical stimulation at the active electrodes, a duration of the electrical stimulation, and a frequency of the electrical stimulation.

16. The device of claim 11, wherein the circuitry comprising the impedance algorithm provides a measurement signal to the plurality of combinations of the electrodes, and assesses responses to the measurement signals, to determine the impedances between the plurality of combinations of the electrodes.

17. The device of claim 16, wherein the measurement signals comprise AC currents, and the responses comprise AC voltages between the plurality of combinations of the electrodes.

18. The device of claim 11, wherein the measured and pre-determined impedance fingerprints comprise values of electrical components in a tissue model between the plurality of combinations of the electrodes.

19. The device of claim 11, wherein the measured and pre-determined impedance fingerprints are indicative of a posture of the patient.

20. The device of claim 19, wherein the database further stores a textual description of the posture with at least some of the pre-determined impedance fingerprints.

21. An implantable stimulator device, comprising:
a plurality of electrodes configured to provide electrical stimulation to a patient;
circuitry comprising an impedance algorithm configured to periodically determine an impedance between a plurality of combinations of the electrodes at a plurality of different frequencies during quiet periods when the electrical stimulation at a first frequency is not occurring, and to determine a measured impedance fingerprint from the determined impedances;
a log configured to store the measured impedance fingerprints; and
a database, wherein the impedance algorithm is further configured to assess the log to identify an impedance fingerprint from the measured impedance fingerprints, and to store that identified impedance fingerprint in a database.

22. The device of claim 21, wherein the determined impedances are complex impedances.

23. The device of claim 21, wherein the identified impedance fingerprint is associated with a stimulation program stored in the database.

24. The device of claim 23, wherein the stimulation program associated with the identified impedance fingerprint in the database comprises (i) default or currently-pending settings associated with the identified in impedance fingerprint, (ii) an average of the stimulation programs associated with the identified impedance fingerprint in the log, or (iii) a last stimulation program associated with the identified impedance fingerprint.

25. The device of claim 23, wherein the stimulation program comprises one or more stimulation parameters, including which electrodes are active, a polarity of the active electrodes, a magnitude of the electrical stimulation at the active electrodes, a duration of the electrical stimulation, and a frequency of the electrical stimulation.

26. The device of claim 21, wherein the circuitry comprising the impedance algorithm provides a measurement signal to the plurality of combinations of the electrodes, and assesses responses to the measurement signals, to determine the impedances between the plurality of combinations of the electrodes.

27. The device of claim 21, wherein the identified impedance fingerprint comprises values of electrical components in a tissue model between the plurality of combinations of the electrodes.

28. The device of claim 21, wherein the identified impedance fingerprint is indicative of a posture of the patient.

29. The device of claim 21, wherein the identified impedance fingerprint is identified by its frequency in the log.

30. The device of claim 29, wherein the identified impedance fingerprint's frequency in the log is determined using statistical metrics.

31. An implantable stimulator device, comprising:
a plurality of electrodes configured to provide electrical stimulation to a patient; and
circuitry comprising an impedance algorithm configured to determine a complex impedance at a plurality of frequencies between at least two of the electrodes during quiet periods when the electrical stimulation at a first frequency is not occurring, wherein the impedance algorithm is further configured to use the determined complex impedances to determine values of electrical components in a tissue model between the two electrodes.

32. The device of claim 31, further comprising a conductive case, and wherein one of the at least two electrodes comprises the case.

33. The device of claim 31, further comprising a lead, wherein at least one of the at least two electrodes is positioned on the lead.

34. The device of claim 31, wherein the circuitry comprising the impedance algorithm provides a measurement signal to the at least two electrodes, and assesses responses to the measurement signals, to determine the impedances between the at least two electrodes.

35. The device of claim 34, wherein the measurement signals comprise AC currents, and the responses comprise AC voltages between the at least two electrodes.

36. An implantable stimulator device, comprising:
a plurality of electrodes configured to provide stimulation to a patient; and
impedance monitoring circuitry for providing a plurality of measurement signals at different frequencies between at least two of the electrodes and for measuring responses between the at least two electrodes in response to the measurement signals during quiet periods when the electrical stimulation at a first frequency is not occurring,
the impedance monitoring circuitry further comprising an impedance algorithm for determining the complex impedance between at least the two electrodes using the measurement signals and the measured responses.

37. The device of claim 36, further comprising a conductive case, and wherein one of the at least two electrodes comprises the case.

38. The device of claim 36, further comprising a lead, wherein at least one of the at least two electrodes is positioned on the lead.

* * * * *